United States Patent
Bianchi et al.

(10) Patent No.: US 7,541,380 B2
(45) Date of Patent: Jun. 2, 2009

(54) USE OF RAPAMYCIN AND STRUCTURAL ANALOGUES THEREOF

(75) Inventors: Nicoletta Bianchi, Mezzogoro (IT); Monica Borgatti, Ferrara (IT); Roberto Gambari, Bologna (IT); Carlo Mischiati, Rovigo (IT)

(73) Assignees: Universita' Degli Studi do Ferrara, Ferrara (IT); Associazione Veneta per la Lotta Alla Talassemia, Rovigo (IT)

( * ) Notice: Subject to any disclaimer, the term of this patent is extended or adjusted under 35 U.S.C. 154(b) by 0 days.

(21) Appl. No.: 10/519,990

(22) PCT Filed: Jul. 3, 2003

(86) PCT No.: PCT/IB03/02632

§ 371 (c)(1),
(2), (4) Date: Jan. 4, 2005

(87) PCT Pub. No.: WO2004/004697

PCT Pub. Date: Jan. 15, 2004

(65) Prior Publication Data

US 2006/0154950 A1  Jul. 13, 2006

(30) Foreign Application Priority Data

Jul. 4, 2002 (IT) .............................. TO02A0582

(51) Int. Cl.
*A61K 31/436* (2006.01)
*A61K 31/785* (2006.01)

(52) U.S. Cl. ................................... 514/433; 424/78.14

(58) Field of Classification Search ....................... None
See application file for complete search history.

(56) References Cited

FOREIGN PATENT DOCUMENTS

WO   WO 0168147 A   9/2001

OTHER PUBLICATIONS

Dickman, et al., Bioorganic and Medicinal Chemistry Letters, 2000, 10, 1405-1408.*
Johnston,et al., Blood, 2001, 98, 410, 1 page (Abstract).*
Rachmilewitz, British Journal of Haematology, 1995, 91, 263-268.*
[Retrieved from] http://cancerweb.ncl.ac.uk/cgi-bin/omd?query=analog, 5 pages, 2005 [retrieved on Jul. 7, 2005].*
Dickman, 2000, Bioorganic and Medicinal Chemistry Letters, 10, 1405-1408.*
G. Rodgers et al., "Novel Treatment Options in the Severe β-Globin Disorders", British Journal of Haematology, 91:263-268, 1995.
J. Rochette et al. "Fetal Hemoglobin Levels in Adults", Blood Reviews, 8:213-224, 1994.
N. Bianchi et al., "Accumulation of γ-globin mRNA and induction of erythroid differentiation after treatment of human leukaemic K562 cells with tallimustine", British Journal of Haematology, 113(4): 951-961; 2001.
Dover et al, "Increased Fetal Hemoglobin in Patients Receiving Sodium 4-Phenylbutyrate", New England Journal of Medicine, 327:569-570, 1992.
Ikuta et al. "Cellular and Molecular Effects of a Pulse Butyrate Regimen and New Inducers of Globin Expression and Hematopoiesis" Annals of New York Academy of Sciences, 850: 87-99, 1998.
Kahan, "Sirolimus: a comprehensive review" Expert Opinion. Nov. 2001; 2(11): 1903-1917.
Dickman et al. "Antifungal Rapamycin Analogues with Reduced Immunosuppressive Activity", Biiorganic & Medicinal Chemistry Letters 10(2000) 1405-1408.
Dell, "Antiproliferative Naphthopyrans: Biological Activity, Mechanistic Studies and Therapeutic Potential", Current Medicinal Chemistry, 1998, 5: 179-194.
Trautmann, et al. "Targeting keratinocyte apoptosis in the treatment of atopic dermatitis and allergic contact dermatitis". Journal of Allergy Clinical Immunology, Nov. 2001 839-846.
Reitamo et al. "Efficacy of Sirolimus (rapamycin) administered concomitantly with a sub therapeutic dose of cyclosporine in the treatment of severe psoriasis: a randomized controlled trial" British Journal of Dermatology, 2001: 145: 438-445.
Guba et al. "Rapamycin inhibits primary and metastasis tumor growth by antiangiogenesis: involvement of vascular endothelial growth factor" National Medical Feb. 2002, vol. 8, No. 2, 128-135.
Garber "Rapamycin's Resurrection: A new way to target the cancer cell cycle" National Cancer Institute, 2001, vol. 93, No. 20, 1517-1519.
Benito et al. "Sirolimus (Rapamycin) for the treatment of refractory acute graft-versus-host disease", Transplantation, vol. 72, No. 12, Dec. 27, 2001, 1924-1929.
Radovancevic et al. "Rapamycin reduces rejection in heart transplant recipients" Transplantation Proceedings, vol. 33, 3321-3222, 2001.
Nishida et al. "Sirolimus (Rapamycin)-Based Rescue Treatment following chronic rejection after liver transplantation" Transplantation Proceedings, 33: 1495 (2001).

(Continued)

*Primary Examiner*—Andrew D Kosar
*Assistant Examiner*—Satyanarayana R Gudibande
(74) *Attorney, Agent, or Firm*—Sughrue Mion, PLLC

(57) ABSTRACT

The use of rapamycin and its structural analogues for the preparation of a medicament for the therapeutic treatment of beta-thalassaemia is described.

1 Claim, No Drawings

OTHER PUBLICATIONS

Bianchi et al. "Induction of Erythroid Differentiation of Human K562 Cells by Cisplatin Analogs" Biochemical Pharmacology vol. 60, 31-40, 2000.

Bianchi et al. "The DNA-binding drugs mithramycin and chromomycin are powerful inducers of erythroid differentiation of human K562 cells". British Journal of Haematology, 1999 104:258-265.

Fibach, "Techniques for Studying Stimulation of Fetal Hemoglobin Production in Human Erythroid Cultures", Hemoglobin, 22(5&A), 445-458, 1998.

Fibach et al. "Hydroxyurea Increases Fetal Hemoglobin in Cultured Erythroid Cells Derived From Normal Individuals and Patients with Sickle Cell Anemia or β-Thalassemia" Blood, vol. 81, No. 6 (Mar. 15), 1993:1630-1963.

Heid et al. "Real Time Quantitative PCR", Genome Research, 6:986-994, 1996.

Gibson et al. "A Novel Method for Real Time Quantitative RT-PCR", Genome Research, 6:995-1001, 1996.

Johnson Julie et al.: "Treatment of beth-thalassemia in the mouse by regulated expression of AAV—encoded erythropoietin" Blood, vol. 98. No. 11 part 2, Nov. 16, 2001, pp. 410b XP009023880.

43rd Annual Meeting of the American Society of Hematology. Part 2: Orlando, Florida< USA; Dec. 7-11, 2001 ISSN: 0006-4971.

WO 0168147 A Bianchi Nicoletta; Feriotto Giordana(IT); Gambari Roberto (IT): m) Sep. 20, 2001 p. 1, Paragraph 1-3, p. 5, Paragraph 1.

\* cited by examiner

USE OF RAPAMYCIN AND STRUCTURAL ANALOGUES THEREOF

The present invention relates to the use of rapamycin and its structural analogues for the therapeutic treatment of beta-thalassaemia.

The existence of substances capable of inducing the expression of the gene for gamma-globin and the biosynthesis of foetal haemoglobin (HbF) in adult subjects has been known for some time (1). In the majority of cases, those substances are also capable of activating or potentiating the transcription of genes for embryonal and foetal globins in experimental model systems.

Recently, for example, numerous DNA-binding molecules have been described that have the capacity to bring about an increase in the expression of genes for gamma-globin (2). Among these there may be mentioned cisplatin and analogues of cisplatin, mithramycin and chromomycin, tallimustine (3). Those molecules are efficient modulators of the expression of genes for gamma-globin.

In human beings, activation of the transcription of genes for gamma-globins in adult subjects leads to the production of foetal haemoglobin mimicking the phenotype HPFH (High Persistence of Foetal Haemoglobin) which confers a favourable clinical picture on patients suffering from beta-thalassaemia also in homozygotic form (4). A therapy providing for the use of those molecules in the treatment of patients suffering from beta-thalassaemia could therefore make those subjects less dependent on transfusion therapy (5).

The present invention is based on the need for novel modifiers of the transcription process that can be used in the treatment of beta-thalassaemia and that have a high level of induction of the expression of gamma-globin genes and a low level of cytotoxicity.

We have surprisingly found that rapamycin, an antibiotic which is described in the prior art and the structural formula of which is illustrated hereinafter, satisfies those requirements.

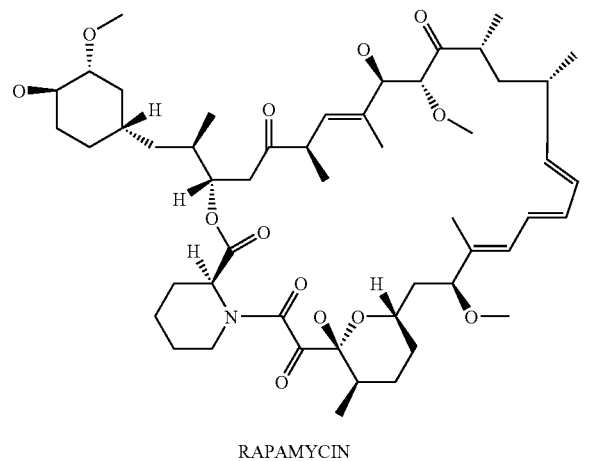

RAPAMYCIN

In particular, it has been found that rapamycin and its structural analogues are capable of activating the expression of the gene for human gamma-globin.

Rapamycin is an antibiotic produced by *Streptomyces hygroscopicus* and originally described as an anti-fungal agent (6).

The chemical synthesis of rapamycin and its structural analogues—for example 7-(N-hydroxy)-acyl, -carbamoyl and -ureide analogues—has been described by various research groups (see, for example, the bibliographical references 7 and 8).

Rapamycin is currently the active ingredient of drugs (Sirolimus, Rapamune, antibiotic AY22989) used as anti-inflammatory agents (9, 10) in the treatment of atopical dermatitis (9), allergic contact dermatitis (9) and psoriasis (10), as anti-tumour agents (11, 12) and anti-fungal agents (6). In addition, rapamycin is widely used in therapy as a drug capable of retarding the rejection process (13) in heart (14), kidney (15) and liver (16) transplants.

However, the capacity of rapamycin and its structural analogues to activate the expression of the human gamma-globin gene has not been described hitherto, nor this activity is attributable to its known effects indicated above.

A first subject of the present invention is therefore the use of rapamycin and its structural analogues for the preparation of a medicament for the therapeutic treatment of beta-thalassaemia.

As has been recently described (17, 18), a combined treatment with various modifiers of the transcription process would also permit a further increase in the expression of genes for gamma-globin.

Therefore, a second subject of the present invention is the use of rapamycin or its structural analogues in combination with at least one further modifier of the transcription process for the preparation of a medicament for the treatment of beta-thalassaemia.

According to a preferred embodiment, said further modifier of the transcription process is selected from the group consisting of cytosine arabinoside, retinoic acid, plicamycin, hydroxyurea, guanine, guanosine triphosphate (GTP), guanosine diphosphate (GDP) and guanosine monophosphate (GMP); of these, cytosine arabinoside and retinoic acid are more preferred.

The activity of rapamycin as an inducer of erythroid cell differentiation and the production of mRNA for gamma-globin was evaluated in human cell cultures. The results of this study are illustrated in the Tables given in the section relating to the Examples. The data obtained indicate that the activity of rapamycin is greater than that of reference drugs (for example, hydroxyurea in the induction of HbF); it has also been ascertained that the cytotoxic effect which may be encountered is much lower than that of hydroxyurea.

The Examples which follow are provided for the purposes of illustration and are not intended to limit the scope of the invention in any way.

EXAMPLE 1

The biological activity of rapamycin was evaluated by examining the capacity of that compound to modulate the expression of genes for gamma-globin in the human cell line K562, which is capable of undergoing erythroid differentiation by expressing genes for gamma-globin if subjected to treatment with modifiers of the biological response that are suitable for the purpose (3, 17, 18). The level of differentiation was evaluated by analysing the positive reaction of the cells to benzidine (3). Some of the data obtained are given in Table 1, which shows the results of six independent experiments (mean±SD). As will be readily appreciated, rapamycin is capable of bringing about an increase in the percentage of K562 cells that react positively to benzidine (40-45% in the treated cells, compared with 4.1% of the control K562 cells). The production of haemoglobin was evaluated by electrophoresis on cellulose acetate and by staining the gel with a solution based on benzidine/$H_2O_2$ (3). The chief haemoglobin produced by K562 cells treated with rapamycin was Hb Portland (alpha2gamma2). The expression of genes coding for gamma-globins was evaluated by quantitative RT-PCR (reverse transcriptase PCR) (3). The data obtained demonstrate an increase in the intracytoplasmic accumulation of mRNA for gamma-globin. These evaluations were carried out after 6 days of induction with 20 nM rapamycin. The results of the quantitative RT-PCR are shown in Table 2.

TABLE 1

| Compound | Concentration (nM) | [a]Erythroid differentiation (%) |
|---|---|---|
| — | — | 4.1 ± 3.7 |
| Rapamycin | 20 | 45.5 ± 5.8 |

[a]Erythroid differentiation = percentage of K562 cells that react positively to benzidine (mean ± SD of 6 experiments).

TABLE 2

| Compound | Concentration (nM) | [b]mRNA for gamma-globin |
|---|---|---|
| — | — | 1 |
| Rapamycin | 20 | 2.4 |

[b]The accumulation of RNA for gamma-globin is given in the Table as an increase compared with that of untreated control K562 cells. The technique used was that of quantitative RT-PCR (21, 22) using the following primer and probe oligonucleotides: gamma-globin forward primer, 5'-TGG CAA GAA GGT GCT GAC TTC-3'; gamma-globin reverse primer, 5'-TCA CTC AGC TGG GCA AAG G-3'; gamma-globin probe 5'-FAM-TGG GAG ATG CCA TAA AGC ACC TGG-TAMRA-3' (FAM = 6-carboxy fluorescein, TAMRA = 6-carboxy-N,N,N',N'-tetramethylrhodamine).

EXAMPLE 2

In order to check whether rapamycin was capable, in addition to inducing K562 cell differentiation, of stimulating the production of mRNA for gamma-globin in human erythroid precursors isolated from peripheral blood, the technique published by Fibach et al. (19, 20) was used. This technique provides for two stages: in the first stage, the cells isolated from peripheral blood of a subject who is healthy or suffering from a haemopoietic pathology, such as sickle cell anaemia or beta-thalassaemia, are sown in a culture medium to which 10% of conditioned medium derived from the vesicle carcinoma cell line 5637 has been added. The second stage consists in cultivating the isolated cells in a suitable culture medium, supplemented by the erythropoietin hormone, 30% foetal bovine serum, 2-mercaptoethanol, albumin, glutamine and desamethasone in order to permit the proliferation and maturing of stem cells of the erythroid type. In this stage the cells can be treated with potential HbF inducers.

For example, in this system it was demonstrated that hydroxyurea, an inhibitor of DNA synthesis currently used in the experimental therapy of beta-thalassaemia, is capable of bringing about the production of HbF.

The results obtained with rapamycin demonstrated an increase in the production of mRNA for gamma-globin in cells treated with rapamycin compared with the same untreated cells (3.75 times), which increase is greater than that which may be encountered using hydroxyurea (Table 3).

TABLE 3

| Compound | Concentration (µM) | [a]mRNA for gamma-globin |
|---|---|---|
| — | — | 1 |
| Rapamycin | 3 | 3.73 |
| Hydroxyurea | 120 | 2.25 |

[a]The accumulation of RNA for gamma-globin is given in the Table as an increase compared with that of untreated control erythroid precursors. The technique used was that of quantitative RT-PCR (21, 22) using the primer and probe oligonucleotides described in Table 2.

BIBLIOGRAPHICAL REFERENCES

1. Rodgers G P, Rachmilewitz E A, British J. Haematology, 91:263-268, 1995.
2. Rochette J, Craig J E and Thein S L, Blood Reviews, 8: 213-224, 1994.
3. Bianchi N, Chiarabelli C, Borgatti M, Mischiati C, Fibach E, Gambari R. Br J Haematol. 113(4):951-61, 2001.
4. Dover, G. J., Brusilow, S and Samid D, New England Journal of Medicine, 327: 569-570, 1992.
5. Ikuta, T., Atweh, G., Boosalis, V., White, G. L., De Fonseca, S., Boosalis, M., Faller, D. V., Perrine, S. P., Annals of New York Academy of Sciences, 850:87-99, 1998.
6. Kahan B D. Sirolimus: a comprehensive review. Expert Opin Pharmacother. 2001 November; 2(11):1903-17.
7. Dickman D A, Ding H, Li Q, Nilius A M, Balli D J, Ballaron S J, Trevillyan J M, Smith M L, Seif L S, Kim K, Sarthy A, Goldman R C, Plattner J J, Bennani Y L. Bioorg Med Chem Lett. 10(13):1405-8, 2000.
8. Dell C P. Curr Med Chem. 5(3):179-94, 1998.
9. Trautmann A, Akdis M, Schmid-Grendelmeier P, Disch R, Brocker E B, Blaser K, Akdis C A. J Allergy Clin Immunol. 108(5):839-46, 2001.
10. Reitamo S, Spuls P, Sassolas B, Lahfa M, Claudy A, Griffiths C E. Br J Dermatol. 145(3):438-45, 2001.
11. Guba M, von Breitenbuch P, Steinbauer M, Koehl G, Flegel S, Hornung M, Bruns C J, Zuelke C, Farkas S, Anthuber M, Jauch K W, Geissler E K. Nat Med. 8(2):128-35, 2002.
12. Garber K. J Natl Cancer Inst. 93(20):1517-9, 2001.
13. Benito A I, Furlong T, Martin P J, Anasetti C, Appelbaum F R, Doney K, Nash R A, Papayannopoulou T, Storb R, Sullivan K M, Witherspoon R, Deeg H J. Transplantation. 72(12):1924-9, 2001.
14. Radovancevic B, El-Sabrout R, Thomas C, Radovancevic R, Frazier O H, Van Buren C. 33(7-8):3221-2, 2001.
15. Podbielski J, Schoenberg L. Prog Transplant. 11(1):29-32, 2001.
16. Nishida S, Pinna A, Verzaro R, Levi D, Kato T, Khan F, Nery J, Weppler D, Tzakis A. Transplant Proc. 33(1-2): 1495, 2001.
17. Bianchi N, Ongaro F, Chiarabelli C, Gualandi L, Mischiati C, Bergamini P, Gambari R. Biochem Pharmacol. 60:31-40, 2000.
18. Bianchi N, Osti F, Rutigliano C, Ginanni Corradini F, Borsetti E, Tomassetti M, Mischiati C, Feriotto G e Gambari R, British Journal of Haematology, 104:258-263, 1999.
19. Fibach E. Hemoglobin, 22: 445-458, 1998.
20. Fibach E, Burke K P, Schechter A N, Noguchi C T & Rodgers G P. Blood, 81: 1630-1635, 1993.
21. Heid C A, Stevens J, Livak K J & Williams P M. Genome Research, 6: 986-994, 1996.

22. Gibson U E, Heid C A & Williams P M. Genome Research, 6: 995-1001, 1996.

The invention claimed is:

1. A method of treating beta-thalassaemia comprising administering a medicament comprising a pharmaceutically effective amount of rapamycin and a transcription process modifier selected from the group consisting of cytosine arabinoside, retinoic acid, plicamycin, mithramycin, hydroxyurea, guanine, guanosine triphosphate (GTP), gaunosine diphosphate (GDP) and guanosine monophosphate (GMP) to a human patient in need of such a treatment.

* * * * *